United States Patent [19]

Kuhr et al.

[11] Patent Number: 4,668,622
[45] Date of Patent: May 26, 1987

[54] PHENOLSULPHONPHTHALEINYL-β-D-GALACTOSIDES AND DIAGNOSTIC AGENTS CONTAINING THEM

[75] Inventors: Manfred Kuhr; Rudolf Machat, both of Mannheim; Wolfgang Weckerle, Grunstadt; Hans-Georg Batz, Tutzing; Rupert Herrmann, Weilheim; Wolfgang Kleeman, Tutzing; Herbert Buschek, Weilheim, all of Fed. Rep. of Germany

[73] Assignee: Boehringer Mannheim GmbH, Mannheim, Fed. Rep. of Germany

[21] Appl. No.: 681,009

[22] Filed: Dec. 13, 1984

[30] Foreign Application Priority Data

Dec. 17, 1983 [DE] Fed. Rep. of Germany ....... 3345748

[51] Int. Cl.$^4$ ........................ C12Q 1/54; C07H 15/00
[52] U.S. Cl. ..................................... 435/14; 536/4.1; 536/17.5; 536/17.9
[58] Field of Search ...................... 536/4.1, 17.5, 17.9; 435/14

[56] References Cited

U.S. PATENT DOCUMENTS 3,953,422 4/1976 Pfeiffer ............................... 536/17.2
4,433,139 2/1984 Ogana et al. ........................ 536/4.1

FOREIGN PATENT DOCUMENTS 2453069 5/1976 Fed. Rep. of Germany ....... 536/4.1

Primary Examiner—Johnnie R. Brown
Assistant Examiner—Elli Peselel
Attorney, Agent, or Firm—Felfe & Lynch

[57] ABSTRACT

The present invention provides phenolsulphonphthaleinyl-β-D-galactosides of the general formula:

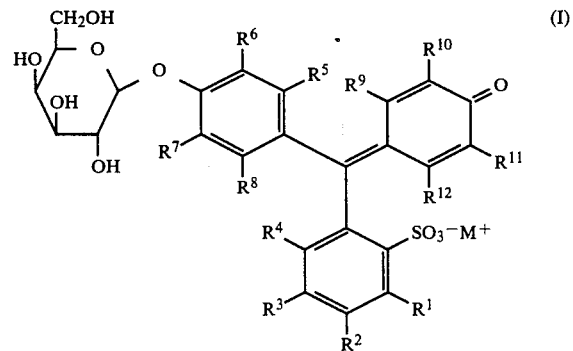

wherein $R^1$ to $R^4$, which can be the same or different, are hydrogen or halogen atoms or nitro or amino groups, $R^5$ to $R^{12}$, which can be the same or different, are hydrogen or halogen atoms or lower alkyl, hydroxyl, lower alkoxy, carboxyl or nitro groups and $M^+$ is a proton, an alkali metal, alkaline earth metal or ammonium ion.

The present invention also provides a process for preparing these galactosides and diagnostic agents containing them.

8 Claims, No Drawings

PHENOLSULPHONPHTHALEINYL-β-D-GALACTOSIDES AND DIAGNOSTIC AGENTS CONTAINING THEM

The present invention is concerned with new phenolsulphonphthaleinyl-β-D-galactosides, a process for the preparation thereof and the use thereof for the determination of β-D-galactosidase.

Oligo- or polysaccharides which contain D-galactose with β-glycosidic bonding occur in almost all organisms. Consequently, the corresponding β-D-galactosidases (EC 3.2.1.23) are also widely occurring and can be detected in numerous micro-organisms, animals and plants.

β-D-galactosidase fulfils a multiple physiological function in mammals. Thus, it plays an important part in carbohydrate metabolism since it brings about the hydrolysis of lactose. Furthermore, β-D-galactosidase is a key enzyme in the breakdown of glycolipids, mucopolysaccharides and glycoproteins.

In recent years, β-D-galactosidase has achieved importance in the field of diagnosis due to its physiological importance. Thus, for example, this enzyme is employed to an increasing extent as an indicator enzyme for enzyme immunoassays (see, for example, Annals of Clinical Biochemistry, 16, 221–240/1979).

Consequently, the determination of the activity of β-D-galactosidase is of increasing importance not only in clinical chemistry but also in diagnosis. For this purpose, quite generally, a galactosidase-containing sample is mixed with an appropriate β-D-galactosidase substrate, the substrate being split by the enzyme, one of the fission products then being detected in an appropriate manner. There can be measured either the glycone liberated by action of the enzyme or the aglycone. As a rule, the latter is determined. As substrate, there can be used the natural substrate lactose, as well as especially a chromogenic galactoside.

Thus, in Biochem. Z., 333, 209/1960, there are described phenyl-β-D-galactoside, as well as some further derivatives substituted on the aromatic ring, for example o-nitrophenyl- and p-nitrophenyl-β-D-galactoside, as substrates of β-D-galactosidase. The phenols liberated by hydrolysis are determined photometrically in the UV range or, in the case of the nitrophenols, in the short-waved, visible wavelength range. An oxidative coupling with aminoantipyrine can also follow as indicator reaction (see Analytical Biochem., 40, 281/1971).

For histochemical investigations, there are used, on the one hand, naphthyl-β-D-galactosides; thus, for example, the 1-naphthyl compound in Histochemie, 35, 199/1973, the 6-bromo-2-naphthyl derivative in J. Biol. Chem., 195, 239/1952 and the naphthol-AS-BI-β-D-galactoside in Histochemie, 37, 89/1973. For visualisation, the naphthols thereby resulting are reacted with various diammonium salts to give azo dyestuffs.

Furthermore, 5-bromo-4-chloroindoxyl-β-D-galactoside is known as a substrate of β-galactosidase. The indicator reaction is here the oxidative dimerisation of the resulting indoxyl to give indigo (Histochemie, 23, 266/1970) or coupling with diazonium salts to give indoxyl azo dyestuffs (Histochemie, 57, 323/1978).

The described methods of determination display considerable disadvantages: on the one hand, they are too insensitive. On the other hand, the substrates used in the histochemical detection are very poorly soluble.

Substantially more sensitive tests result when, as substrates, galactosides are used, the aglycone of which can be detected fluorometrically. Thus, in Proc. Nat. Acad. Sci. US, 47, 1981/1961, fluorescein di-β-D-galactoside is described as a substrate. Furthermore, use can be made of 2-naphthyl-β-D-galactoside (Analytical Biochem., 42, 275/1971) or of 4-methyl-umbelliferyl-β-D-galactoside (Biochem. J., 102, 525/1967).

A disadvantage of the fluorometrical methods is the considerable expense of the apparatus which has to be used.

Therefore, there is still a need for substrates with which β-D-galactosidase can be determined simply, quickly and dependably.

We have now found that β-D-galactosidase can be detected very sensitively and visually in the visible spectral range or with a simple spectral photometer apparatus when using sulphonphthaleinyl-β-D-galactosides as substrates. Furthermore, these compounds have the advantage that they are very easily water-soluble.

Consequently, according to the present invention, there are provided sulphonphthaleinyl-β-D-galactosides of the general formula:

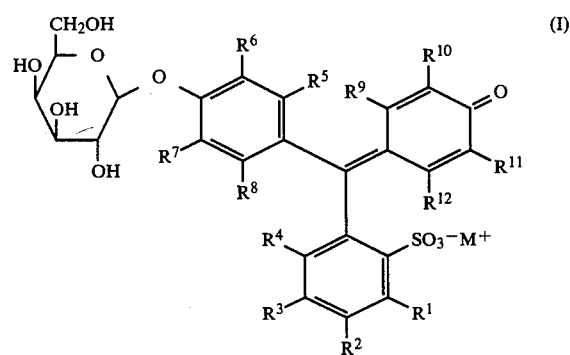

wherein $R^1$ to $R^4$, which can be the same or different, are hydrogen or halogen atoms or nitro or amino groups, $R^5$ to $R^{12}$, which can be the same or different, are hydrogen or halogen atoms or lower alkyl, hydroxyl, lower alkoxy, carboxyl or nitro groups and $M^+$ is a proton or an alkali metal, alkaline earth metal or ammonium ion.

All the sulphonphthaleinyl-β-D-galactosides of the general formula I are new compounds. They can be prepared by methods known from carbohydrate chemistry.

Preferably, phenolsulphonphthaleins of the general formula:

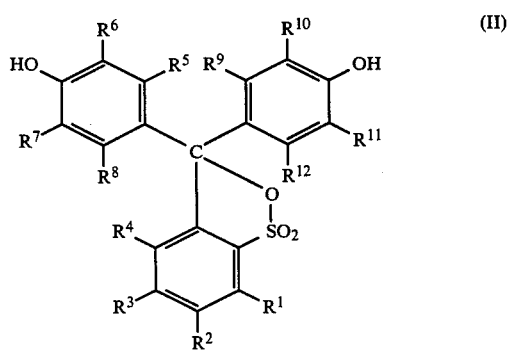

wherein $R^1$ to $R^{12}$ have the above-given meanings, are reacted in known manner with per-O-substituted-1-halogeno-α-D-galactoses of the general formula:

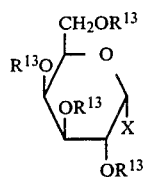

(III)

in which X is a halogen atom and $R^{13}$ is a protective group conventional in carbohydrate chemistry, with Walden inversion of the C-1 atom of the sugar residue to give per-O-substituted sulphonphthaleinyl-β-D-galactosides of the general formula:

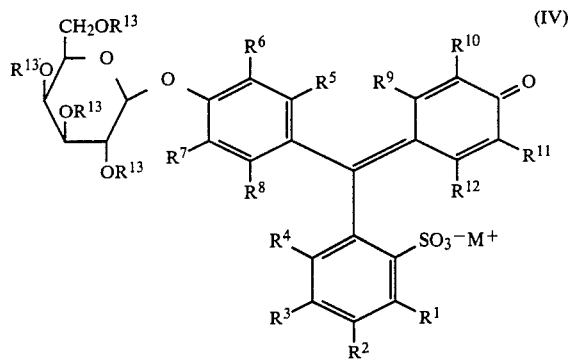

(IV)

and the protective groups $R^{13}$ are split off from the latter in known manner.

The reaction of the compounds of general formulae II and III to give galactosides of general formula IV is preferably carried out in the presence of an acid acceptor, such as an alkali metal hydroxide or carbonate, in aqueous acetone or, under phase transfer conditions, in a water/benzene or water/chloroform mixture.

Furthermore, the galactosides of general formula IV can be prepared by first converting the phenolsulphonphthaleins of general formula II by means of an alkali metal hydroxide or alcoholate into a dialkali metal salt or by means of an optionally substituted amine into an ammonium salt, whereafter these are then reacted in a dipolar aprotic solvent, such as acetone, dimethyl sulphoxide, dichloromethane, tetrahydrofuran or dimethylformamide, with the per-O-substituted 1-halogenogalactoses of general formula III.

Furthermore, in the case of the synthesis of galactosides of general formula IV from the phenol-sulphonphthaleins of general formula II and the 1-halogalactoses of general formula III, additions of individual silver salts or mixtures of silver salts (silver oxide, silver carbonate, silver carbonate on Celite, silver triflate or silver salicylate) and/or of individual mercury salts or mixtures of mercury salts (mercury bromide, cyanide, acetate or oxide), optionally with the use of drying agents, such as calcium chloride or Drierite, in solvents, such as methylene chloride, chloroform, benzene, toluene or dioxan, have proved to be useful.

The so-obtained per-O-substituted sulphonphthaleinyl-β-D-galactosides of general formula IV are also new compounds.

The splitting off of the protective groups $R^{13}$ from the per-O-substituted sulphonphthaleiny-β-D-galactosides of general formula IV to give the sulphonphthaleinyl-β-D-galactosides of general formula I is carried out according to the conventional methods in carbohydrate chemistry (see, for example, Advanced Carbohydrate Chem., 12, 157/1957), for example in the case of acyl protective groups by means of sodium methylate or barium methylate or ammonia in methanol.

The phenolsulphonphthaleins of the general formula II are either known, commercially available substances or can be prepared by known processes from the corresponding phenol and the corresponding o-sulphonbenzoic acid (see, for example, D. S. Breslow and H. Skolnik, in A. Weissberger. The Chemistry of Heterocyclic Compounds, Interscience Publishers, New York, 1966, Volume 21, p. 118) or, starting from known sulphonphthaleins, by subsequent derivatisation, for example by halogenation or nitration (cf., for example, D. S. Breslow and H. Skolnik, ibid., pp. 141 and 144).

The per-O-substituted 1-halogeno-α-D-galactoses of general formula III employed as starting materials are also known compounds. They are described, for example, in Chem. Ber., 35, 836/1902; Nature, 165, 369/1950; Acta chem. Scand., Ser. B, 33, 116/1979; J. Chem. Soc., 1419/1965; and Carbohydr. Res., 11, 85/1969.

By halogen in the definitions of $R^1$ to $R^{12}$ and X is to be understood fluorine, chlorine, bromine and iodine and, in the case of $R^1$ to $R^{12}$, preferably fluorine, chlorine and bromine and, in the case of X, preferably chlorine and bromine.

The lower alkyl radical in the definitions of $R^5$ to $R^{12}$ contains 1 to 5 and preferably 1 to 3 carbon atoms, the methyl and isopropyl radicals being especially preferred.

The lower alkoxy radical in the definitions of $R^5$ to $R^{12}$ contains 1 to 5 and preferably 1 to 3 carbon atoms, the methoxy radical being especially preferred.

The alkali metal ion in the definition of $M^+$ is to be understood to be the lithium, sodium or potassium ion, lithium and sodium ions being preferred.

The alkaline earth metal ion in the definition of $M^+$ signifies the magnesium, calcium and barium ion, the calcium ion being preferred.

The ammonium ion in the definition of $M^+$ is to be understood to be a radical of general formula $[NR^{14}R^{15}R^{16}R^{17}]^+$, wherein $R^{14}$ to $R^{17}$, which can be the same or different, signify hydrogen atoms or lower alkyl radicals containing 1 to 4 and preferably 1 or 2 carbon atoms, or benzyl radicals.

The protective group $R^{13}$ conventional in carbohydrate chemistry is especially preferably an acetyl, benzoyl, benzyl or trimethylsilyl radical.

The present invention is also concerned with the use of the new sulphonphthaleinyl-β-D-galactosides of general formula I for the determination of the activity of β-D-galactosidase. Furthermore, the present invention provides diagnostic agents for the determination of the activity of β-D-galactosidases, which agents contain the new sulphonphthaleinyl-β-D-galactosides of general formula I.

The use of the new sulphonphthaleinyl-β-D-galactosides as substrates for β-D-galactosidase gives β-D-galactosidase test systems which are much more sensitive than those previously known. The new substrates can be advantageously used for the determination of the activity of β-D-galactosidases, not only in the biochemical field but also in the clinical-chemical field since they are more sensitive. From this result several advantages:

(a) Smaller β-D-galactosidase activities can be measured.

(b) Smaller amounts of sample can be employed.

(c) The determination of the β-D-galactosidase activity can take place in a considerably shorter time.

(d) Furthermore, the small sample use and the favourable measurement wavelength reduce the susceptibility to disturbance of the method due to other components present in the sample.

We have found that the new substrates can be used for the determination of the activity of β-D-galactosidases of any origin and which can differ in their optimum pH value. In such cases, too, diagnostic agents containing substrates of general formula I react much more sensitively than the previously known test agents.

The sulphonphthaleinyl-β-D-galactosides of general formula I can also be used for immunological methods of determination in which β-D-galactosidase is used as indicator enzyme, the activity of which must be determined after carrying out of the immunological reaction. Such immunological methods of determination with an enzymatic indicator reaction are known as enzyme immunoassays. These methods serve for the determination of the concentration of proteins, polysaccharides, hormones, pharmaceuticals and other low molecular substances in the range of $10^{-5}$ to $10^{-12}$ mole/liter. Depending upon the requirement of phase separation steps, a differentiation is made between a homogeneous and a heterogeneous carrying out of the tests. A further subdivision can take place into competitive and non-competitive test principles.

However, all test principles work with enzyme-antigen or enzyme-antibody conjugates. The enzymatic indicator reaction is common to all enzyme immunoassays.

An indicator enzyme which can be used for such purposes is β-D-galactosidase. The determination of β-D-galactosidase in such enzyme immunoassays usually takes place by adding an appropriate β-D-galactosidase substrate thereto, which is enzymatically split and measured photometrically in the usual way.

Consequently, an improvement of the β-D-galactosidase test system also leads to considerable advantages in the case of such enzyme immunoassays:

1. Here, too, a higher sensitivity makes possible a further lowering of the detection limits, shorter reaction times and smaller sample use and thus also smaller disturbances by other components of the sample.

2. The more favourable measurement wavelength reduces, in the case of certain carryings out of reaction, the susceptibility to disturbance of the methods by insoluble components, for example by turbidities.

Besides one or more of the substrates of general formula I according to the present invention, the diagnostic agent contains an appropriate buffer system, as well as possibly further appropriate additional materials conventionally used for such diagnostic agents, for example wetting agents, stabilisers and the like. The diagnostic agent can be present in the form of a solution, a lyophilisate, a powder mixture or a reagent tablet or can be applied to an absorbent carrier.

The diagnostic agent according to the present invention in the form of a solution preferable contains all reagents required for the test. As solvent, there can be used water or a mixture of water with a water-soluble organic solvent, for example methanol, ethanol, acetone or dimethylformamide. For reasons of storage stability, it can be advantageous to divide up the reagents required for the test into two or more solutions which are first mixed immediately before carrying out the actual investigation.

For the preparation of the diagnostic agent in the form of a lyophilisate with a total weight of, in each case, about 5 to 20 mg. and preferably of about 10 mg., a solution is dried which, besides all the reagents needed for the test, contains conventional structural formers, for example polyvinylpyrrolidone, and optionally further filler materials, for example mannitol, sorbitol or xylitol.

A diagnostic agent in the form of a powder mixture or of a reagent tablet can be produced by mixing the components of the test with conventional galenical additive materials and granulated. Additive materials of this kind include, for example, carbohydrates, such as mono-, oligo- and polysaccharides, sugar alcohols, such as mannitol, sorbitol and xylitol, and other soluble inert compounds, such as polyethylene glycols and polyvinylpyrrolidone. In general, the powder mixtures or reagent tablets have an end weight of about 30 to 200 mg. and preferably of 50 to 80 mg.

For the production of the diagnostic agents in the form of a test strip, an absorbent carrier, preferably filter paper, cellulose or synthetic fibre fleece, is impregnated with solutions of the necessary reagents usually employed for the production of test strips in readily volatile solvents, for example water, methanol, ethanol or acetone. This can take place in one impregnation step. However, it is often preferable to carry out the impregnation in several steps, solutions being used which each contain some of the components of the diagnostic agent. Thus, for example, in a first step, impregnation can be carried out with an aqueous solution which contains the buffer and other water-soluble additive materials and then, in a second step, with a solution which contains the β-D-galactosidase substrate. The finished test papers can be used as such or, in known manner, can be stuck on to handles or preferably sealed between synthetic materials and fine meshworks according to Federal Republic of Germany Patent Specification No. 2,118,445.

The following Examples illustrate some of the numerous process variants which can be used for the synthesis of the new compounds according to the present invention, as well as, by way of example, the use of the new sulphonphthaleinyl-β-D-galactosides for the determination of the activity of β-D-galactosidase.

The following abbreviations are used in the Examples:

HEPES: 2-[4-(2-hydroxyethyl)-1-piperazinyl]-ethane-sulphonic acid
BSA: bovine serum albumin
Tween-20: polyoxyethylene(20)sorbitan monolaurate
Tricin: [N-tris-(hydroxymethyl)]-methyl-glycine.

EXAMPLE 1

3,3'-Dichlorophenolsulphonphthaleinyl-β-D-galactoside sodium salt (a)

A solution of 45 g. (0.11 mole) 2,3,4,6-tetra-O-acetyl-α-D-galactopyranosyl bromide in 450 ml. chloroform is warmed to 60° C. While stirring at this temperature, there are added a solution of 29.9 g. (0.11 mole) benzyl triethylammonium bromide in 114 ml. 1.25N aqueous sodium hydroxide solution (0.142 mole), followed by 46.5 g. (0.11 mole) 3,3'-dichlorophenolsulphonphthalein (chlorophenol red). Residues of the dyestuffs are rinsed down from the walls of the reaction vessel used with some water and a further 114 ml. 1.25N aqueous sodium hydroxide solution.

The reaction mixture is boiled under reflux for 12 hours and thereafter left to stand for 8 hours at ambient temperature. The organic phase is separated off and the aqueous phase is shaken several times with chloroform. For the removal of starting material still present, the combined organic phases are shaken several times with 0.1N aqueous sodium hydroxide solution.

After washing the chloroform phase with water and drying with anhydrous sodium sulphate, the organic solvent is evaporated. The residue is triturated with diethyl ether to give 46 g. 3,3′-dichlorophenolsulphonphthaleinyl-2,3,4,6-tetra-O-acetyl-β-D-galactoside sodium salt as a yellow amorphous material (yield: 54% of theory); m.p. 190° C. (decomp.).

NMR: (DMS0-d$_6$): 1.95 (s, 3H), 1.99 (s, 3H), 2.02 (s, 3H), 2.12 (s, 3H), 4.0–4.6 (m, 4H), 5.1–5.7 (m, 3H), 6.1–6.8 (m, 1H), 6.9–7.7 (m, 8H), 7.8–8.0 (m, 1H).

(b)

A solution of 28 g. (0.036 mole) of the tetraacetylgalactoside prepared according to (a) in 270 ml. anhydrous methanol is cooled to 0°–5° C. For desacetylation, 72 ml. of a 1 molar (0.072 mole) sodium methylate solution in methanol are added thereto, while stirring at this temperature.

After 15 minutes at 0°–5° C., the solution is mixed with about 300 ml. Amberlite IRC 50 for the removal of excess sodium ions and the mixture is stirred for 2 hours at 5° C. After filtering off the ion exchanger with suction, this is washed several times with methanol.

After evaporation of the combined filtrates, the residue is purified by column chromatography on silica gel with methylene chloride/methanol (5/1 v/v) to give 12 g. 3,3′-dichlorophenolsulphonphthaleinyl-β-D-galactoside sodium salt as a yellow, amorphous powder (yield: 55% of theory); m.p. 210° C. (decomp.).

NMR: (DMSO-d$_6$): 3.3–3.7 (m, 6H), 3.9–5.0 (m, 4H), 5.1 (d, J=7 Hz, 1H), 6.1–6.8 (m, 1H), 6.9–7.6 (m, 8H), 7.8–8.0 (m, 1H).

EXAMPLE 2

In a manner analogous to that described in Example 1, by the reaction of 2,3,4,6-tetra-O-acetyl-α-D-galactopyranosyl bromide with the phenolsulphonphthaleins given below under "starting material", there are prepared, via the corresponding peracetylated galactosides, the β-D-galactosides given under "end product":

| | starting material | end product | m.p. in °C. |
|---|---|---|---|
| (1) | phenol red | phenolsulphonphthaleinyl-β-D-galactoside sodium salt | 218–220 |
| (2) | fluorophenol red | 3,3′-difluorophenolsulphonphthaleinyl-β-D-galactoside sodium salt | glass-like |
| (3) | chlorophenol blue | 3,3′,5,5′-tetrachlorophenolsulphonphthaleinyl-β-D-galactoside sodium salt | 145–150 |
| (4) | pyrocatechol violet | 3,3′-dihydroxyphenolsulphonphthaleinyl-β-D-galactoside sodium salt | 115–120 |
| (5) | iodophenol blue | 3,3′,5,5′-tetraiodophenolsulphonphthaleinyl-β-D-galactoside sodium salt | 210–215 |
| (6) | m-cresol purple | 2,2′-dimethylphenolsulphonphthaleinyl-β-D-galactoside sodium salt | 205–209 |
| (7) | bromocresol purple | 3,3′-dibromo-5,5′-dimethylphenolsulphonphthaleinyl-β-D-galactoside sodium salt | 200–203 |
| (8) | o-cresol red | 3,3′-dimethylphenolsulphonphthaleinyl-β-D galactoside sodium salt | 200–204 |
| (9) | thymol blue | 3,3′-diisopropyl-6,6′-dimethylphenolsulphonphthaleinyl-β-D-galactoside sodium salt | 205–209 |
| (10) | bromothymol blue | 3,3′-dibromo-5,5′-diisopropyl-2,2′-dimethylphenolsulphonphthaleinyl-β-D-galactoside sodium salt | 190–195 |
| (11) | salicyl red | 3,3′-dicarboxyphenolsulphonphthaleinyl-β-D-galactoside sodium salt | 178–180 |
| (12) | 3,3′,5,5′-tetrabromo-2,2′-dimethylphenolsulphonphthalein | 3,3′,5,5′-tetrabromo-2,2′-dimethylphenolsulphonphthaleinyl-β-D-galactoside sodium salt | 100–103 |
| (13) | 3,3′-dinitrophenolsulphonphthalein | 3,3′-dinitrophenolsulphonphthaleinyl-β-D-galactoside sodium salt | 167–170 |
| (14) | 3,3′-dichloro-5,5′-dinitrophenolsulphonphthalein | 3,3′-dichloro-5,5′-dinitrophenolsulphonphthaleinyl-β-D-galactoside sodium salt | 115–118 |
| (15) | 3,3′-dimethyl-5,5′-dinitrophenolsulphonphthalein | 3,3′-dimethyl-5,5′-dinitrophenolsulphonphthaleinyl-β-D-galactoside sodium salt | 155–158 |
| (16) | 3,3′-dimethoxyphenolsulphonphthalein | 3,3′-dimethoxyphenolsulphonphthaleinyl-β-D-galactoside | |
| (17) | 3,3′-difluorophenyl-3″,4″,5″,6″-tetrabromosulphonphthalein | 3,3′-difluorophenyl-3″,4″,5″,6″-tetrabromosulphonphthaleinyl-β-D-galactoside | |
| (18) | 2,2′-dimethyl-3,3′-dinitrophenolsulphonphthalein | 2,2′-dimethyl-3,3″-dinitrophenolsulphonphthaleinyl-β-D-galactoside | |
| (19) | 2,2′-dimethyl-5,5′-dinitrophenolsulphonphthalein | 2,2′-dimethyl-5,5′-dinitrophenolsulphonphthaleinyl-β-D-galactoside | |
| (20) | phenol-4″-nitrosulphonphthalein | phenol-4″-nitrosulphonphthaleinyl-β-D-galactoside sodium salt | 300 |
| (21) | phenol-5″-nitrosulphonphthalein | phenol-5″-nitrosulphonphthaleinyl-β-D-galactoside | |
| (22) | 3,3′-dichlorophenol-4″-nitrosulphonphthalein | 3,3′-dichlorophenol-4″-nitrosulphonphthaleinyl-β-D-galactoside sodium salt | 160/300 |
| (23) | 3,3′-difluorophenol-4″-nitrosulphonphthalein | 3,3′-difluorophenol-4″-nitrosulphonphthaleinyl-β-D-galactoside | |
| (24) | 3,3′,4″-trinitrophenolsulphonphthalein | 3,3′,4″-trinitrophenolsulphonphthaleinyl-β D-galactoside sodium salt | 300 |

EXAMPLE 3

3,3'-Difluorophenolsulphonphthaleinyl-β-D-galactoside sodium salt (a)

6.2 g. (0.016 mole) 3,3'-difluorophenolsulphonphthalein (fluorophenol red) are dissolved in 170 ml. anhydrous methanol. For the formation of the disodium salt, 32 ml. (0.032 mole) of a 1 molar sodium methylate solution in methanol are added thereto. The solution is then evaporated to dryness. For dissolving the residue in 140 ml. anhydrous dimethylformamide, 7.3 g. (0.0176 mole) 2,3,4,6-tetra-O-acetyl-α-D-galactopyranosyl bromide are added thereto, followed by stirring for 6 hours at ambient temperature. After suction filtration, the filtrate is evaporated at ambient temperature under oil pump vacuum. The residue is triturated with diethyl ether, filtered off with suction and dried to give 6.9 g. 3,3'-difluorophenolsulphonphthaleinyl-2,3,4,6-tetra-O-acetyl-β-D-galactoside sodium salt as an orange-coloured amorphous material (yield 63% of theory); m.p. 215° C. (decomp.).

NMR: (DMSO-$d_6$): 1.94 (s, 3H), 1.96 (s, 3H), 1.99 (s, 3H), 2.15 (s, 3H), 3.9–4.7 (m, 4H), 5.0–5.6 (m, 3H), 6.2–6.6 (m, 1H), 7.0–7.6 (m, 8H), 7.9–8.2 (m, 1H).

(b)

A solution of 3.5 g. (0.005 mole) of the tetraacetylgalactoside prepared according to (a) in 750 ml. anhydrous methanol is mixed at ambient temperature with 1.5 ml. (0.0015 mole) of a 1 molar sodium methylate solution in methanol. After standing overnight, the solution is evaporated. The residue is purified by column chromatography on silica gel with methylene chloride/methanol (5/1 v/v) to give 1.2 g. 3,3'-difluorophenolsulphonphthaleinyl-β-D-galactoside sodium salt as an orange-red, hygroscopic, amorphous powder (yield 41% of theory).

NMR: (DMSO-$d_6$): 3.1–3.9 (m, 6H), 4.1–5.3 (m, 4H), 4.95 (d, J=7 Hz, 1H), 6.2–6.6 (m, 1H), 6.8–7.6 (m, 8H), 7.8–8.0 (m, 1H).

EXAMPLE 4

In a manner analogous to that described in Example 3, from 2,3,4,6-tetra-O-acetyl-α-D-galactopyranosyl bromide and the phenolsulphonphthaleins stated below under "starting material", there are prepared the β-D-galactosides mentioned under "end product":

| starting material | end product | m.p. °C. |
| --- | --- | --- |
| (1) phenol red | phenolsulphonphthaleinyl-β-D-galactoside sodium salt | 208–212 |
| (2) o-cresol red | 3,3'-dimethylphenolsulphonphthaleinyl-β-D-galactoside sodium salt | 202–205 |
| (3) bromocresol purple | 3,3'-dibromo-5,5'-dimethylphenolsulphonphthaleinyl-β-D-galactoside sodium salt | 198–202 |

EXAMPLE 5

3,3'-Dibromo-5,5'-dimethylphenolsulphonphthaleinyl-β-D-galactoside sodium salt (a)

A solution of 11.03 g. (0.027 mole) 2,3,4,6-tetra-O-acetyl-α-D-galactopyranosyl bromide and 5.6 g. (0.007 mole) bromocresol purple tribenzylammonium salt in 60 ml. dichloromethane is mixed with 3.1 g. (0.013 mole) silver oxide and 3.7 g. (0.013 mole) silver carbonate and stirred for 12 hours at ambient temperature. After filtering off the precipitate, the filtrate is evaporated and the residue is purified by column chromatography on silica gel with toluene/ethyl acetate/methanol (1/1/0.2 v/v/v). Evaporation of the appropriate fraction gives 4.4 g. 3,3'-dibromo-5,5'-dimethylphenolsulphonphthaleinyl-2,3,4,6-tetra-O-acetyl-β-D-galactoside tribenzylammonium salt as a yellow, amorphous material (yield 54% of theory).

NMR: (DMSO-$d_6$): 1.8–2.3 (m, 18H), 3.8–4.4 (m, 4H), 5.2–5.6 (m, 9H), 6.6–8.1 (m, 23H).

(b)

A solution of 4 g. (0.0035 mole) of the tetraacetylgalactoside prepared according to (a) in 40 ml. anhydrous methanol is cooled to −40° C. and, for desacetylation, mixed with 15.5 ml. of a 1M (0.015 mole) sodium methylate solution.

After one hour, the solution is neutralised by treatment with about 30 ml. Amberlite LRC 50 (H form) and evaporated. The residue is purified by column chromatography on silica gel with methylene chloride/methanol/acetone (6/2/1 v/v/v) to give 2 g. 3,3'-dibromo-5,5'-dimethylphenolsulphonphthaleinyl-β-D-galactoside sodium salt as a yellow, amorphous powder (yield 62% of theory); m.p. 200°–203° C. (decomp.).

NMR: (DMSO-$d_6$): 1.9–2.4 (m, 6H), 3.2–4.0 (m, 6H), 4.4 (m, 2H), 4.8 (m, 2H) [after deuterium exchange: 4.9 (d, J=7 Hz, 1H)], 6.7–8.1 (m, 8H).

EXAMPLE 6

In a manner analogous to that described in Example 5, there are prepared from 2,3,4,6-tetra-O-acetyl-α-D-galactopyranosyl bromide and (1)

fluorophenol red
3,3'-difluorophenolsulphonphthaleinyl-β-D-galactoside sodium salt;
hygroscopic glass.

(2)

phenol-3",4",5",6"-tetrabromosulphonphthalein
phenol-3",4",5",6"-tetrabromosulphonphthaleinyl-β-D-galactoside sodium salt;
m.p. 215° C. (decomp).

(3)

3,3',5,5'-tetrachlorophenol-3",4",5",6"-tetrabromosulphonphthalein
3,3',5,5'-tetrachlorophenol-3",4",5",6"-tetrabromosulphonphthaleinyl-β-D-galactoside sodium salt;
m.p. 150° C. (decomp.).

(4)

phenol-4"-nitrosulphonphthalein phenol-4″-nitrosulphonphthaleinyl-β-D-galactoside sodium salt;
m.p. >300° C.

(5)

3,3′-dichlorophenol-4″-nitrosulphonphthalein
3,3′-dichlorophenol-4″-nitrosulphonphthaleinyl-β-D-galactoside sodium salt;
double m.p. 160° C./>300° C.

(6)

3,3′-dimethylphenol-4″-nitrosulphonphthalein
3,3′-dimethylphenol-4″-nitrosulphonphthaleinyl-β-D-galactoside sodium salt;
m.p. 210°–220° C.

(7)

3,3′,4″-trinitrophenolsulphonphthalein
3,3′,4″-trinitrophenolsulphonphthaleinyl-β-D-galactoside sodium salt;
m.p. >300° C.

(8)

phenol-4″-aminosulphonphthalein
phenol-4″-aminosulphonphthaleinyl-β-D-galactoside sodium salt;
lyophilisate (amorphous).

EXAMPLE 7

3,3′-Difluorophenolsulphonphthaleinyl-β-D-galactoside tribenzylammonium salt

A solution of 6.77 g. (0.01 mole) fluorophenol red tribenzylammonium salt and 5.3 g. (0.01 mole) per-O-trimethylsilyl-α-D-galactopyranosyl bromide in 70 ml. dichloromethane are mixed with 1.15 g. (0.005 mole) silver oxide and 1.4 g. (0.005 mole) silver carbonate and stirred for 18 hours with the exclusion of moisture. After filtering off the precipitate, the filtrate is evaporated and the residue is, for splitting off the protective groups, taken up in 60 ml. methanol and kept for 12 hours at ambient temperature. For purification, it is chromatographed over silica gel with dichloromethane/methanol (5/1 v/v) to give 1.2 g. 3,3′-difluorophenolsulphonphthaleinyl-β-D-galactoside tribenzylammonium salt as an orange coloured, amorphous powder (yield 14% of theory); m.p. 157°–165° C.

NMR: (DMSO-$d_6$): 3.1–3.9 (m, 6H), 4.2–5.2 (m, 11H), 6.3 (m, 1H), 6.8–7.6 (m, 23H), 7.9 (m, 1H).

EXAMPLE 8

3,3′-Dichlorophenolsulphonphthaleinyl-β-D-galactoside lithium salt 1.5 g. (0.0025 mole) 3,3′-dichlorophenolsulphonphthaleinyl-β-D-galactoside sodium salt, prepared according to Example 1, is dissolved in a little water. The solution is applied to a column filled with Amberlite IR 120 (Li form). Lyophilisation of the eluate gives 1.4 g. 3,3′-dichlorophenolsulphonphthaleinyl-β-D-galactoside lithium salt as an orange coloured, amorphous powder (yield: 96% of theory); m.p. 190° C. (decomp.).

NMR: (DMSO-$d_6$): 3.3–3.8 (m, 6H), 4.3–4.9 (m, 4H), 5.07 (s, J=7 Hz, 1H), 6.1–7.7 (m, 9H), 7.8–8.1 (m, 1H).

EXAMPLE 9

In a manner analogous to that described in the Example 8, there are prepared from 3,3′-dichlorophenolsulphonphthaleinyl-β-D-galactoside sodium salt (see Example 1)

(a)

by exchange chromatography on Amberlite IR 120 in the Ca form
3,3′-dichlorophenolsulphonphthaleinyl-β-D-galactoside calcium salt
orange-red, amorphous product (yield: 78% of theory); m.p. 250° C. (decomp.).

NMR: (DMSO-$d_6$): 3.2–3.8 (m, 6H), 4.4–5.1 (m, 4H), 5.1 (s, J=7 Hz, 1H), 6.2–7.6 (m, 9H), 7.8–8.0 (m, 1H).

(b)

By exchange chromatography on Amberlite IR 120 in the (H$_3$C)$_4$N form
3,3′-dichlorophenolsulphonphthaleinyl-β-D-galactoside tetramethylammonium salt
yellow, amorphous product (yield 85% of theory); m.p. 190°–195° C.

NMR: (DMSO-$d_6$): 3.2 (s, 12H), 3.3–4.0 (m, 6H), 4.1–5.3 (m, 4H), 5.1 (d, J=7 Hz, 1H), 6.4 (m, 1H), 7.0–7.7 (m, 8H), 7.9 (m, 1H).

EXAMPLE 10

3,3′-Dichlorophenolsulphonphthaleinyl-β-D-galactoside tribenzylammonium salt 1.5 g. (0.0025 mole) 3,3′-dichlorophenolsulphonphthaleinyl-β-D-galactoside sodium salt (see Example 1) is dissolved in a little water and passed through a column filled with Amberlite IR 120 (H form). The eluate is mixed with a stoichiometric (0.72 g.) amount of tribenzylamine dissolved in 15 ml. ethanol and evaporated. There is obtained 1.7 g. 3,3′-dichlorophenolsulphonphthaleinyl-β-D-galactoside tribenzylammonium salt as a yellow, amorphous material (yield 78% of theory); m.p. 140°–150° C.

EXAMPLE 11

In a manner analogous to that described in Example 10, there is prepared from 3,3′-dichlorophenolsulphonphthaleinyl-β-D-galactoside sodium salt (see Example 1), with the use of benzyldiethylamine, the corresponding
3,3′-dichlorophenolsulphonphthaleinyl-β-D-galactoside benzyldiethylammonium salt
yellow, amorphous powder (yield 69% of theory); m.p. 245°–248° C.

EXAMPLE 12

Determination of the activity of β-D-galactosidase (a)

Preparation of the solutions used

Buffer solution:
HEPES: 100 mmol/liter
sodium chloride: 154 mmol/liter
magnesium L-aspartate: 2 mmol/liter
BSA: 10 g./liter
Tween-20: 0.5 g./liter
pH value (adjusted with aqueous sodium hydroxide: 7.3 (37° C.)
solution
Reagent Solution 1:
In the above-described buffer solution are dissolved 5 mmol/liter phenolsulphonphthaleinyl-β-D-galactoside sodium salt. The pH value is adjusted with aqueous sodium hydroxide solution to pH 8.5 (37° C.).

Reagent Solution 2:

In the above-described buffer solution are dissolved 5 mmol/liter 3,3'-difluorophenolsulphonphthaleinyl-β-D-galactoside sodium salt. The pH value is adjusted with aqueous sodium hydroxide solution to pH 7.5 (37° C.).

Reagent Solution 3:

In the above-described buffer solution are dissolved 5 mmol/liter 3,3'-dichlorophenolsulphonphthaleinyl-β-D-galactoside sodium salt. The pH value of the buffer solution of 7.3 (37° C.) is maintained.

Reagent Solution 4:

In the above-described buffer solution are dissolved 5 mmol/liter 3,3',5,5'-tetrachlorophenol-3",4",5",6"-tetrabromosulphonphthaleinyl-β-D-galactoside sodium salt. The pH value of the buffer solution of 7.3 (37° C.) is maintained.

The substrate concentration and the pH values are to be optimised for each substrate used. Therefore, quite knowingly, different values for substrate concentrations or pH values can occur in the individual reagent solutions.

Enzyme solution:

Commercially available β-D-galactosidase from *Escherichia coli* is dissolved in the above-mentioned buffer solution. The activity of this solution is about 0.08 U/ml. (referred to the statements of the manufacturer).

(b)

Carrying out of the measurements

The measurement takes place photometrically, in each case at the wavelength given below.

950 μl. of reagent are mixed in a 1 cm. cuvette at 37° C. with 50 μl. of enzyme solution. As a measure for the reaction, there is determined the extinction increase per unit time in [mExt/min]. It is calculated from the measured extinction by division with the reaction time.

The following Table gives the measurement values found:

| Reagent No. | Measurement wavelength [nm] | reaction [mExt/min] |
|---|---|---|
| 1 | 560 | 9 |
| 2 | 578 | 71 |
| 3 | 578 | 123 |
| 4 | 578 | 121 |

EXAMPLE 13

Determination of the activity of β-D-galactosidase (a)

Preparation of the solutions used

Buffer solution:
HEPES: 50 mmol/liter
citric acid: 50 mmol/liter
tricin: 50 mmol/liter
sodium chloride: 154 mmol/liter
magnesium L-aspartate: 1 mmol/liter
BSA: 10 g./liter
pH value (adjusted with aqueous sodium hydroxide solution): 6.9 (37° C.)

Reagent Solution 1:

In the above-described buffer solution are dissolved 5 mmol/liter 3,3'-dimethylphenolsulphonphthaleinyl-β-D-galactoside.

Reagent Solution 2:

In the above-described buffer solution are dissolved 5 mmol/liter 3,3'-dihydroxyphenolsulphonphthaleinyl-β-D-galactoside.

Enzyme solution:

Commercially available β-D-galactosidase from *Escherichia coli* is dissolved in the above-mentioned buffer solution. The activity of this solution is about 0.08 U/ml. (referred to the statements of the manufacturer).

(b)

Carrying out of the measurements

950 μl. of reagent are mixed in a 1 cm. cuvette at 37° C. with 50 μl. of enzyme solution. After 10 minutes reaction time, it is adjusted to pH 10 with aqueous sodium hydroxide solution and the extinction measured. The same procedure is used for a blank containing buffer instead of enzyme solution. During the reaction and the measurement, the temperature is kept at 37° C. From the extinctions determined on the batches with and without enzyme, there is calculated the extinction difference. By division of this extinction difference by the reaction time, there is given, as measure for the reaction, the extinction increase per unit time in [mExt/min].

The following Table gives the measurement values found:

| Reagent No. | Measurement wavelength [nm] | reaction [mExt/min] |
|---|---|---|
| 1 | 578 | 98 |
| 2 | 593 | 6 |

EXAMPLE 14

Determination of the activity of β-D-galactosidases of differing origin

There are used commercially available β-D-galactosidase preparations of differing origin. As a characteristic feature, these manifest their maximum activity at differing pH values:

Statements of the manufacturer:
from beans (jack beans): pH 3.5
from *Aspergillus niger*: pH 4.0
from *Escherichia coli*: pH 6.9
from bovine liver: pH 7.3

(a)

Preparation of the solutions used

Buffer solution:
HEPES: 50 mmol/liter
citric acid: 50 mmol/liter
tricin: 50 mmol/liter
sodium chloride: 154 mmol/liter
magnesium L-aspartate: 1 mmol/liter
BSA: 10 g./liter Solutions are prepared of the above composition with differing pH values according to the pH optima of the β-D-galactosidases (pH 3.5/4.0/6.9/7.3), the pH values being adjusted at 37° C. with hydrochloric acid or aqueous sodium hydroxide solution.

Reagent solutions:

In the above-mentioned buffer solutions with the differing pH values of 3.5/4.0/6.9/7.3 are dissolved, in each case, 5 mmol/liter 3,3'-dichlorophenolsulphonphthaleinyl-β-D-galactoside sodium salt.

Enzyme solutions:

The β-D-galactosidases are dissolved in the buffers with, in each case, the optimum pH values:
from beans (jack beans): in buffer of pH 3.5
from *Aspergillus niger*: in buffer of pH 4.0
from *Escherichia coli*: in buffer of pH 6.9
from bovine liver: in buffer of pH 7.3

The activity of these solutions is about 0.08 U/ml. (referred to the statements of the manufactuer).

(b)

Carrying out of the measurements

The enzyme reaction takes place during a definite reaction time at the optimum pH value for the particular enzyme. 1000 μl. of reagent are mixed in a 1 cm. cuvette at 37° C. with 30 μl. of an enzyme solution. After 15 minutes reaction time, it is adjusted with aqueous sodium hydroxide solution to pH 8.5 and the extinction determined at 578 nm. During the reaction and the measurement, the temperature is kept constant at 37° C. In the same way, for each measurement a blank is carried out. For this purpose, instead of the enzyme solution, there are used 30 μl. of buffer solution.

(c)

Evaluation

First, there is obtained the difference between the measurement value with the enzyme and the measurement value of the blank. By division of this difference by the reaction time, there is determined, as measure for the reaction, the extinction increase per unit time in [mExt/min].

measurement value (with enzyme) −
measurement value (blank) = Δ measurement value $$\frac{\Delta \text{ measurement value}}{\text{reaction time}} = \text{reaction } [mExt/\text{min}]$$

The measurement values found for the reaction of the individual enzymes are given in the following Table:

| enzyme from | pH value | reaction speed [mExt/min] |
|---|---|---|
| beans (jack beans) | 3.5 | 71 |
| *Aspergillus niger* | 4.0 | 112 |
| *Escherichia coli* | 6.9 | 74 |
| bovine liver | 7.3 | 32 |

The above-described experimental results show that the sulphophthaleinyl-β-D-galactosides can be used as substrates for β-D-galactosidases of any origin.

EXAMPLE 15

Determination of the activity of free and conjugated β-D-galactosidase (a)

Preparation of the solutions used

Buffer solution:
HEPES: 100 mmol/liter
sodium chloride: 154 mmol/liter
magnesium L-aspartate: 2 mmol/liter
BSA: 10 g./liter
Tween-20: 0.5 g./liter
pH value (adjusted with aqueous sodium hydroxide solution): 7.3 (37° C.)

Reagent solution:

In the above-described buffer solution are dissolved 5 mmol/liter 3,3'-dichlorophenolsulphonphthaleinyl-β-D-galactoside sodium salt. The pH value of the buffer solution of 7.3 (37° C.) is maintained.

Enzyme solution:

Commercially available β-D-galactosidase from *Escherichia coli* is dissolved in buffer. The activity of this solution is about 0.08 U/ml. (referred to the statements of the manufacturer).

Enzyme conjugate solution:

A β-D-galactosidase-antibody preparation is used. The preparation of such an enzyme-antibody conjugate is known. It is described, for example, in Biochem. Biophys. Acta 612, 40–49/1980. The preparation is so diluted with buffer that there is obtained an activity approximately comparable to that of the above-described enzyme solution.

(b)

Carrying out of the measurement

The measurement takes place photometrically at 578 nm. 950 μl. of reagent solution are, in each case, mixed in a 1 cm. cuvette at 37° C. with 50 μl. of enzyme solution or with 50 μl. of enzyme conjugate solution. As a measure for the reaction, there is determined the extinction increase per unit time in [mExt/min].

For the reaction with the free β-D-galactosidase there are measured 124 mExt/min and for the reaction with β-D-galactosidase-antibody conjugate 120 mExt/min.

Both measurement values show that a very readily measurable extinction difference is found not only with free but also with conjugated β-D-galactosidase. From this it follows that the new sulphonphthaleinyl-β-D-galactosides can be used in the same way as substrates not only for free β-D-galactosidase but also for β-D-galactosidase conjugates. Thus, the new substrates can be used not only as diagnostic agents for the determination of free β-D-galactosidases but can also be used in an advantageous manner in the case of enzyme immunoassays in which β-D-galactosidase is used as indicator enzyme.

It will be understood that the specification and examples are illustrative but not limitative of the present invention and that other embodiments within the spirit and scope of the invention will suggest themselves to those skilled in the art.

What is claimed is:

1. A phenosulphonphthaleinyl-beta-D-galactosides of the formula:

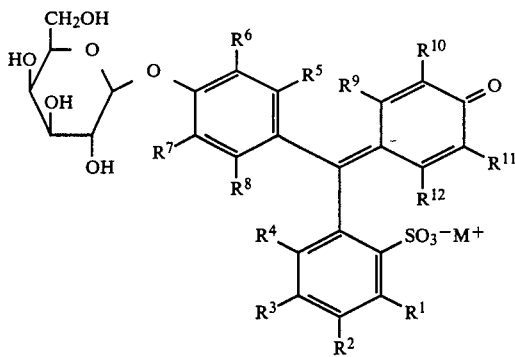

wherein
- $R^1$ to $R^4$, are individually selected from the group consisting of hydrogen, fluorine, chlorine, bromine, iodine, nitro and amino;
- $R^5$ to $R^{12}$ are individually selected from the group consisting of hydrogen, fluorine, chlorine, bromine, iodine, lower alkyl of 1 to 5 carbon atoms, hydroxyl, lower alkoxy of 1 to 5 carbon atoms, carboxyl and nitro groups; and
- $M^+$ is a proton, an alkali metal selected from the group consisting of lithium, sodium, and potassium, an alkaline earth metal selected from the group consisting of magnesium, calcium and barium, or an ammonium ion.

2. The phenolsulphonphthaleinyl-beta-D-galactosides claimed in claim 1 wherein at least one of $R^1$ to $R^{12}$ is fluorine, chlorine or bromine.

3. The phenolsulphonphthaleinyl-beta-D-galactosides claimed in claim 1 wherein the alkali metal is lithium or sodium.

4. The phenolsulphonphthaleinyl-beta-D-galactosides claimed in claim 1 wherein the alkaline earth metal is calcium.

5. The phenolsulphonphthaleinyl-beta-D-galactosides claimed in claim 1 wherein the lower alkyl has 1 to 3 carbon atoms and the lower alkoxy has 1 to 3 carbon atoms.

6. The phenolsulphonphthaleinyl-beta-D-galactosides claimed in claim 1 wherein the lower alkyl is methyl or isopropyl.

7. The phenolsulphonphthaleinyl-beta-D-galactosides claimed in claim 1 wherein the lower alkoxy is methoxy.

8. In a diagnostic agent for the detection of beta-D-galactosidase of the type containing a chromogenic substrate, and a buffer substance, the improvement comprising, as the chromogenic substrate, a phenolsulphonphthaleinyl-beta-D-galactoside as claimed in claim 1.

* * * * *

UNITED STATES PATENT AND TRADEMARK OFFICE
CERTIFICATE OF CORRECTION

PATENT NO. : 4,668,622
DATED : May 26, 1987
INVENTOR(S) : Manfred Kuhr et al.

It is certified that error appears in the above-identified patent and that said Letters Patent is hereby corrected as shown below:

[75] Inventors: "Kleeman" should read -- Kleemann --

Col. 3, line 67 "sulphonphthaleiny-β-D-" should read -- sulphonphthaleinyl-β-D- --

Col. 6, line 42 "2,118,445" should read -- 2,118,455 --

Col. 8, line 68 insert the following at end of table

-- (25) phenol-4"-amino-sulphonphthalein  phenol-4"-aminosulphonphthaleinyl-β-D-galactoside sodium salt  amorphous --

Col. 15, line 57, "sulphophthaleinyl" should read -- sulphonphthaleinyl --

Signed and Sealed this

Twelfth Day of April, 1988

Attest:

DONALD J. QUIGG

*Attesting Officer*   *Commissioner of Patents and Trademarks*